US008187320B2

(12) United States Patent
Wnendt et al.

(10) Patent No.: US 8,187,320 B2
(45) Date of Patent: May 29, 2012

(54) MEDICAL IMPLANTS CONTAINING FK506 (TACROLIMUS)

(75) Inventors: Stephan Wnendt, Aachen (DE);
Randolf Von Oepen, Tuebingen (DE);
Bernd Kuttler, Reutlingen (DE);
Gerhard Lang, Sulz (DE); Guenter Lorenz, Tuebingen (DE); Axel Grandt, Strassberg (DE)

(73) Assignees: Abbott Laboratories Vascular Enterprises Limited, Dublin (IE);
Astellas Pharma Inc., Tokyo (JP)

( * ) Notice: Subject to any disclaimer, the term of this patent is extended or adjusted under 35 U.S.C. 154(b) by 1006 days.

(21) Appl. No.: 10/641,787

(22) Filed: Aug. 15, 2003

(65) Prior Publication Data
US 2004/0117008 A1 Jun. 17, 2004

Related U.S. Application Data

(63) Continuation-in-part of application No. PCT/EP02/01707, filed on Feb. 18, 2002.

(30) Foreign Application Priority Data

Feb. 16, 2001 (DE) .................................. 101 07 339
Jun. 5, 2001 (DE) .................................. 101 27 011
Jun. 6, 2001 (DE) .................................. 101 27 330

(51) Int. Cl.
*A61F 2/82* (2006.01)
(52) U.S. Cl. .................. 623/1.42; 623/1.1; 623/1.39
(58) Field of Classification Search ................ 623/1.42, 623/1.43, 1.44, 1.46, 1.47, 1.38, 23.64, 23.7, 623/23.67; 427/2.25; 424/422
See application file for complete search history.

(56) References Cited

U.S. PATENT DOCUMENTS

| 5,246,445 | A |   | 9/1993  | Yachia et al. |
| 5,411,552 | A |   | 5/1995  | Andersen et al. |
| 5,443,458 | A |   | 8/1995  | Eury |
| 5,443,498 | A |   | 8/1995  | Fontaine |
| 5,449,382 | A |   | 9/1995  | Dayton |
| 5,464,450 | A |   | 11/1995 | Buscemi et al. |
| 5,500,013 | A |   | 3/1996  | Buscemi et al. |
| 5,690,670 | A | * | 11/1997 | Davidson ............... 623/1.15 |
| 5,795,591 | A |   | 8/1998  | Lee et al. |
| 5,824,049 | A | * | 10/1998 | Ragheb et al. ........... 623/1.44 |
| 5,836,966 | A |   | 11/1998 | St. Germain |
| 5,843,172 | A |   | 12/1998 | Yan |
| 5,882,335 | A |   | 3/1999  | Leone et al. |
| 5,902,266 | A |   | 5/1999  | Leone et al. |
| 5,922,729 | A | * | 7/1999  | Chang et al. ............ 514/291 |

(Continued)

FOREIGN PATENT DOCUMENTS

CA   2235031   10/1998

(Continued)

OTHER PUBLICATIONS

U.S. Appl. No. 60/394,978, filed Jul. 8, 2002, Grandt.

(Continued)

*Primary Examiner* — David Isabella
*Assistant Examiner* — Suba Ganesan
(74) *Attorney, Agent, or Firm* — Workman Nydegger

(57) ABSTRACT

Implants and methods of making same are provided for treatment or prophylaxis of coronary or peripheral vascular constrictions or vascular occlusions, and particularly, stenoses or restenoses, that comprise FK506 in chemically covalently bound, non-covalently bound or physically immobilized form.

29 Claims, 7 Drawing Sheets

U.S. PATENT DOCUMENTS

| | | | |
|---|---|---|---|
| 5,972,027 A | 10/1999 | Johnson | |
| 6,071,305 A | 6/2000 | Brown et al. | |
| 6,214,042 B1 | 4/2001 | Jacobsen et al. | |
| 6,471,980 B2 | 10/2002 | Sirhan et al. | |
| 6,613,083 B2 | 9/2003 | Alt | |
| 6,685,745 B2 | 2/2004 | Reever | |
| 6,709,451 B1 | 3/2004 | Noble et al. | |
| 6,752,829 B2 | 6/2004 | Kocur et al. | |
| 6,758,859 B1 | 7/2004 | Dang et al. | |
| 6,776,796 B2 | 8/2004 | Falotico et al. | |
| 6,833,353 B1 * | 12/2004 | Yamamoto et al. | 514/9 |
| 7,052,488 B2 | 5/2006 | Uhland | |
| 2002/0038146 A1 | 3/2002 | Harry | |
| 2002/0087209 A1 | 7/2002 | Edwin et al. | |
| 2003/0083646 A1 | 5/2003 | Sirhan et al. | |
| 2003/0170287 A1 * | 9/2003 | Prescott | 424/423 |
| 2004/0133270 A1 | 7/2004 | Grandt | |

FOREIGN PATENT DOCUMENTS

| | | |
|---|---|---|
| DE | 19744135 | 3/1999 |
| DE | 19781971 | 9/1999 |
| DE | 19910188 | 5/2000 |
| EP | 1057460 | 12/1987 |
| EP | 0633032 | 6/1994 |
| EP | 0923953 | 6/1998 |
| EP | 0970711 A2 * | 6/1999 |
| WO | WO9001969 | 3/1990 |
| WO | WO9626682 | 9/1996 |
| WO | WO 00/03677 * | 1/2000 |
| WO | WO0121229 | 3/2001 |
| WO | WO 02/065947 | 8/2002 |
| WO | WO2004004602 | 1/2004 |

OTHER PUBLICATIONS

U.S. Appl. No. 10/616,125, Mar. 1, 2005, Office Action.
U.S. Appl. No. 10/616,125, Nov. 4, 2005, Office Action.
U.S. Appl. No. 10/616,125, Jul. 5, 2006, Office Action.
U.S. Appl. No. 10/616,125, Jan. 8, 2007, Office Action.
U.S. Appl. No. 10/616,125, Apr. 24, 2007, Office Action.
U.S. Appl. No. 10/616,125, Sep. 26, 2007, Office Action.
U.S. Appl. No. 10/616,125, Apr. 15, 2008, Office Action.
U.S. Appl. No. 10/616,125, Oct. 30, 2008, Office Action.
U.S. Appl. No. 10/616,125, Jun. 9, 2009, Office Action.
U.S. Appl. No. 10/616,125, Jan. 19, 2010, Office Action.
U.S. Appl. No. 10/616,125, Jun. 22, 2011, Office Action.

* cited by examiner

Drug content after dipping in drug solution of polymer coated stents

MEDICAL IMPLANTS CONTAINING FK506 (TACROLIMUS)

FIELD OF THE INVENTION

The present invention relates to implants for the treatment or prophylaxis of coronary or peripheral vascular occlusions or vascular constrictions that comprise FK506 (Tacrolimus) in chemically covalently bound or non-covalently bound or physically immobilized form, processes for the production thereof and to the use thereof.

BACKGROUND OF THE INVENTION

The formation of arteriosclerotic lesions in arterial blood vessels is the underlying disease for a large range of clinical symptoms which extend from angina pectoris via intermittent claudication to myocardial infarction and ischemic stroke; all based on atheroma formation and/or stenotic lesions. The term stenotic lesions refers to the local reduction of the vascular lumen to less than 60-70% of its normal diameter, which in turn leads to a marked reduction in the supply of oxygen and nutrients to the particular tissue. Although pharmacotherapy (statins, ACE inhibitors, gpIIa/IIIb blockers and plasminogen activators) have shown good therapeutic results especially in the area of cardiovascular diseases in recent decades, surgical interventions (bypass operations, etc.) are still necessary for many patients who have developed a complete ischemic state. These operations are moreover relatively complicated and costly and involve the risk of serious complications.

Minimally invasive surgical methods have been developed in order to prevent the development of ischemic heart diseases. The invention of percutaneous transluminal coronary angioplasty (PCTA) in the late 1970s was a great breakthrough in cardiology. PTCA involves the use of inflatable balloons which are advanced as far as the stenotic lesion in the coronary arteries. These balloons are then inflated at the particular target positions and achieve dilatation of the stenotic region. A similar procedure can also be used for dilation of carotid or peripheral arteries.

Despite this, it was found relatively soon that a recurrent stenosis developed in a relatively large proportion of PTCA patients at the sites which had been dilated with the balloon catheter. It was discovered in this connection that this so-called restenosis arises through reorganization of the vascular architecture of the tissue layers. The introduction of tubular vascular metal implants, so-called stents, in the transluminal treatment of stenosis improved the situation. It has been demonstrated in clinical studies (Serruys et al., N. Engl. J. Med. 331 (1994) 489-495) that the use of stents at the balloon-dilated sites was able to reduce the occurrence of restenosis from about 45% to about 30%. Although this is to be regarded as a significant improvement in the prevention of residual restenosis, there is still a distinct stimulus for therapeutic improvements.

It was discovered in detailed studies of the pathophysiology of restenosis in the stent that this differs from PTCA-induced restenosis. Inflammatory reactions, hyperproliferation and in-migration of smooth muscle cells (SMCs) are important factors in neointima formation which lead to restenosis in the stent. It has been found in the animal model of restenosis and even in human tissue that the hyperproliferation of the SMCs is associated with infiltration of macrophages and T cells into the tissue around the reinforcements of the stent (Grewe et al., J. Am. Coll. Cardiol. 35 (2000) 157-63).

In analogy to other clinical indications where inflammatory reactions and hyperproliferation of cells are involved and which can be controlled by medical treatment, attempts have also been made to treat restenosis by pharmacotherapy. Selected active agents have been given either orally or intravenously or brought to the site of action through perforated catheters. Unfortunately, to date none of these active agents have been able to reduce restenosis significantly (Gruberg et al., Exp. Opin. Invest. Active agents 9 (2000) 2555-2578).

Direct delivery of pharmacologically active agents from active agent-coated stents is one active area of investigation. Animal experiments and initial results of clinical trials with active agent-coated stents give the impression that delayed release of immunosuppressive and/or antiproliferative active agents can reduce the risk of restenosis. Paclitaxel, a cytotoxic active agent, and rapamycin, an immunosuppressive and cytostatic active agent, have been tested in animal experiments. Both compounds are reported to inhibit neointima formation (Herdeg et al., Semin Intervent Cardiol 3 (1998) 197-199; Hunter et al., Adv. Active agent. Delivery Rev. 26 (1997) 199-207; Burke et al., J. Cardiovasc Pharmacol., 33 (1999) 829-835; Gallo et al., Circulation 99 (1999) 2164-2170). Nevertheless, the beneficial effect has been observed to cease after 6 months of implantation of coated stents in pigs with paclitaxel (Heldman, International Local Active agent Delivery Meeting and Cardiovascular Course on Radiation, Geneva, Jan. 25-27, 2001).

Rapamycin showed good efficacy with complete abolition of restenosis in initial clinical applications (Sousa et al., Circulation 103 (2001) 192-195). On the other hand, this agent delays healing of vessel wall injury caused by balloon angioplasty and stent implantation.

In view of the foregoing, it would be desirable to provide medical implants that balance the effects of healing of the arterial vessel wall after angioplasty and stent placement with controlling neointima formation.

It further would be desirable to provide active agents that achieve this balance by selectively interfering with specific mechanisms leading to neointima formation.

It would also further be desirable to provide implants with favorable properties for the treatment and prophylaxis of restenosis.

SUMMARY OF THE INVENTION

The present invention seeks to obtain a balance between healing of the arterial vessel wall after angioplasty and stent placement and controlling neointima formation. In order to achieve this balance, active agents are selected that selectively interfere with specific mechanisms leading to neointima formation.

As used in this specification, as applies to every active agent mentioned herein for the purposes of this invention (including FK506), the term "active agent" includes direct derivatives of the active agent, and the active agent also in all types of salts, enantiomers, racemates, bases or free acids of the active agent, and mixtures thereof.

It is therefore an object of the invention to provide implants with favorable properties for the treatment and prophylaxis of restenosis.

In one preferred embodiment, the present invention comprises medical implants including FK506, also known as Tacrolimus, in chemically covalently or noncovalently bound or physically immobilized form, and optionally, at least one other active agent.

It is further preferred that the implant be an intracavernous, more preferably an intravascular, implant. As used herein, "intracavernous" means inside a cavity or hollow organ, such as blood vessels, gullets, ureters, bile ducts etc. As used herein, "intravascular" means use in a blood vessel.

It is also preferred for the implant to be suitable for the treatment or prophylaxis of coronary or peripheral vascular constrictions or occlusions, in particular of constrictions or stenoses or restenoses, preferably for the prophylaxis of restenosis.

Particularly preferred therefore is an intracavernous, preferably intravascular, implant for the treatment or prophylaxis of coronary or peripheral vascular constrictions or occlusions, in particular of constrictions or stenoses or restenoses, preferably for the prophylaxis of restenosis, comprising FK506 in chemically covalently or noncovalently bound or physically immobilized form, and, optionally, at least one other active agent.

BRIEF DESCRIPTION OF THE DRAWINGS

The above and other objects and advantages of the present invention will be apparent upon consideration of the following detailed description, taken in conjunction with the accompanying drawings, in which.

DETAILED DESCRIPTION OF THE INVENTION

Overview of the Invention

Figure 1:
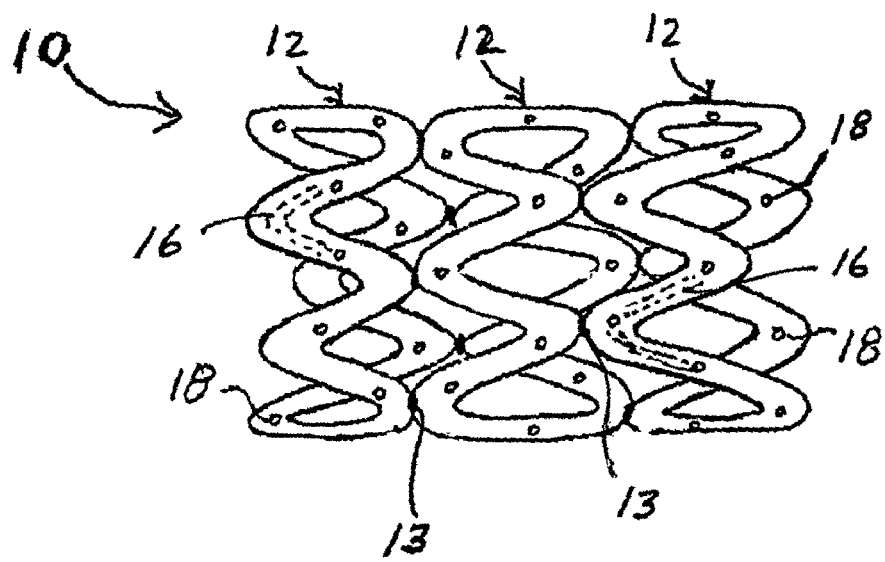
FIG. 1 is a perspective view of a stent having FK506 loaded into internal reservoir and released through passageways that communicate with the exterior of the stent.

The present invention provides medical implants, and methods of making and using same, which provide a balance between healing of the arterial vessel wall after angioplasty and stent placement and controlling neointima formation. This balance is achieved by selecting active agents that selectively interfere with specific mechanisms leading to neointima formation. The active agent also is chosen to be suitable for the treatment or prophylaxis of coronary or peripheral vascular constrictions or occlusions, in particular of constrictions or stenoses or restenoses, preferably for the prophylaxis of restenosis.

In a preferred embodiment, the present invention comprises medical implants including Tacrolimus, also known as FK506, in chemically covalently or noncovalently bound or physically immobilized form, and, optionally, at least one other active agent.

The macrolide antibiotic FK506 (tacrolimus, [3S-[3R*[E(1S*, 3S*, 4S*)], 4S*, 5R*,-8S*, 9E, 12R*, 14R*, 15S*, 16R*, 18S*, 19S*, 26aR*]]-5,6,8,11,12, 13, 14, 15, 16, 17, 18, 19, 24, 25, 25, 26, 26a-hexadecahydro-5,19-dihydroxy-3-[2-(4-hydroxy-3-methoxycyclohexyl)-1-methylethenyl]-14,16-dimethoxy-4,10,12,18-tetramethyl-8-(2-propenyl)-15,19-epoxy-3H-pyrido[2,1-c] [1,4]oxaazacyclotricosine-1, 7-20,21(4H,23H)-tetrone; Merck index No. 9000) is an active agent developed for transplantation medicine.

FK506 inhibits the release of interleukin-2 (IL-2) and interferon-γ (IFN-γ) from T cells and thus blocks rejection of an implant (graft) (Wiederrecht et al., Ann. NY Acad Sci. 696 (1993) 9-19). FK506 has also been investigated in SMC cultures with a view to. inhibition of the proliferation of smooth muscle cells (Mohacsi et al., J. Heart Lung Transplant. 16 (1997) 484-492; Marx et al., Circulation Res., 76 (1995) 412-417) and migration thereof (Poon et al., J. Clin. Invest. 98 (1996) 2777-2283).

In general, FK506 has been assessed by various researchers as unsuitable, because of its low potency, for the prevention of restenosis (Mohacsi et al. (1997); Poon et al. (1996); Marx et al., 1995; Dell, Curr Med Chem 5 (1998) 179-94). Mohacsi et al. found a half-maximal inhibition of SMC proliferation between 100 nM and 1 µM, while Marx et al. observed no effect at all at concentrations up to 123 nm. In contrast thereto, rapamycin is active in inhibiting the proliferation of SMC cultures in the nanomolar concentration range.

In view of the foregoing literature, there could be little expectation that FK506 would be useful for inhibiting restenosis (Mohacsi et al. (1997); Poon et al. (1996)). However, contrary to the reported literature, the present inventors have observed that the use of FK506 as part of a stent or other implant can be effective in the treatment and prophylaxis of restenosis. Specifically, local administration of FK506 has been observed to provide a useful balance between preventing restenosis and re-endothelialization of the injured vessel wall.

Without it being possible to assume such beneficial activity from the outset, the observed beneficial effects might possibly be explained due to immunomodulatory activity of FK506, which is shown by a half-maximal inhibition of IL-2 release at concentrations around 0.1 nM (Kino et al., J. Antibiot. 40 (1987) 1256-1265) and an inhibitory effect on SMC proliferation at concentrations around 300-500 nM. The use of FK506 is therefore favorable.

Glossary

As used in this specification, the following terms are given the following meanings:

"Peripheral" refers in particular to vessels or other hollow organs outside the heart and the coronary vessels.

"Chemically noncovalently" bound means linkages through interactions such as hydrogen bonds, hydrophobic interactions, Van der Waals forces, etc.

"Physically immobilized" means that the active agent is enclosed, e.g. via a membrane in a hole, or steric entrapment through choice of the orifice sizes.

"Implant" means any type of artificial object which is introduced (even for only a limited time) into the human body intracavernously, and includes, without limitation, stents, grafts, stent grafts, graft connectors, guide wires, catheter pumps or catheters.

"Stent" means an elongate implant with a hollow interior and at least two orifices and usually a circular or elliptical, but also any other, cross section (mostly made of metal, but, optionally, also of plastic materials or bio-polymers, e.g., synthetic polymers or organic material, such as cartilage, preferably with a perforated, lattice-like structure that is implanted into vessels, in particular blood vessels, to restore and maintain the vessels patent and functional.

"Graft" means an elongate implant with a hollow interior and with at least two orifices and usually circular or elliptical, but also any other, cross section and with at least one closed polymer surface which is homogeneous or, optionally, woven from various strands. The surface preferably is impermeable to corpuscular constituents of blood and/or for water, so that the implant serves as a vascular prosthesis and is usually employed for damaged vessels or in place of vessels. Preferably the polymer used in for the implants is selected from Dacron; polytetrafluoroethylene (PTFE/Teflon), expandable or non-expandable; or polyurethane; preferably from polytetrafluoroethylene (PTFE), expandable or non-expandable; or polyurethane.

"Stent graft" means a connection between a stent and a graft. A stent graft preferably comprises a vascular prosthesis reinforced with a stent (both as defined above), wherein a polymer layer is homogeneous or, optionally, woven from various strands and is impermeable for corpuscular constituents of blood and/or for water. More preferably, the stent has on at least 20% of its surface a perforated (lattice-like), preferably metallic, outer layer and at least one closed polymer layer that is located inside or outside the stent outer layer. The closed polymer layer may be homogeneous or, optionally, woven from various strands, and is impermeable for corpuscular constituents of blood and/or for water. Optionally, where the closed polymer layer is disposed inside the metallic outer layer, a further perforated (lattice-like), preferably metallic, inner layer may be located inside the polymer layer.

"Graft connector" means an implant that connects at least two hollow organs, vessels or grafts, consists of the materials defined for grafts or stent grafts and/or has the structure defined for the latter. Preferably, a graft connector has at least two, three or four, orifices, arranged, for example, as an asymmetric "T" shape.

"Catheter" means a tubular instrument intended for introduction into hollow organs. More preferably, a catheter may be designed for use in guiding other catheters, or for angiography, ultrasound imaging, or balloon catheters for dilatation or stent delivery.

"Catheter pump" means a catheter provided on its tip with a propeller able to assist the pumping of the myocardium.

"Metal" or "metal alloy" means steel or steel alloys or nickel or nickel alloys.

"Perforated structures" mean, in particular, lattice-like or woven or plaited ones.

"Nanocapsules" mean the coating of micellar systems or colloidal solids to give ultrafine particles with a solid coating. The coated particles, whose size is in the nanometer range, form colloidal solutions.

"Microparticles" mean globular synthetic carriers produced by special polymerization processes (e.g., emulsion, suspension and particle polymerization processes), wherein the carriers have a size in the range from 0.1-100 μm up to 1 mm.

Preferred Implants of the Invention

In accordance with the principles of the present invention, medical implants, and methods of making same, are provided that enable local administration of FK506. The FK506 may be mechanically or chemically bound to the implant by any of a variety of mechanisms, including direct deposition on the exterior of the implant; by loading the FK506 into recesses formed in an exterior surface of the implant; by loading the FK506 into the voids or pores of a ceramic coating disposed on the exterior surface of the implant; by loading the FK506 into an interior reservoir of an implant that communicates with an exterior of the implant via one or more passageways; by applying the FK506 in a resinous form to an implant delivery system; or by binding the FK506 to a polymeric cover or coating of the implant.

In one preferred embodiment, the implant comprises at least one closed or perforated layer or surface comprising a metal or a metal alloy and that is homogeneous or formed from various strands. An exterior surface of the implant may be treated so that the FK506 adheres to or within recesses formed in the exterior of the implant. Alternatively, the exterior surface of the implant may comprise a ceramic or polymeric coating having pores that serve as a reservoir from which the FK506 is released.

As a further alternative, the implant may have a closed layer that defines a reservoir into which the FK506 is loaded and then subsequently released via one or more passageways or channels that communicate with the exterior of the implant. As a still further alternative, the closed or perforated layer or surface of the implant may comprise a polymer that is homogeneous or formed from various strands.

In another preferred embodiment, the implant has at least one polymer layer that covers completely or partly a closed or perforated layer or surface that consists of a metal or a metal alloy and is homogeneous or formed from various strands, preferably an optionally lattice-like structure consisting of a metal or a metal alloy.

In a further preferred embodiment, the implant has at least one closed or perforated layer or surface that includes a metal or a metal alloy and is homogeneous or formed from various strands, and at least one closed or perforated layer or surface that includes a polymer and is homogeneous or formed from various strands.

More preferably, the implant of the present invention comprises a metal or a metal alloy (optionally a lattice-like structure) and/or for the layer or surface comprising a polymer to be homogeneously closed or woven and/or to be water- and/or corpuscle-impermeable. Preferably, the sequence of layers and surfaces for the implant (from the outside to the inside) comprises metal-polymer, polymer-metal, metal-polymer-metal or polymer-metal-polymer. The layer or surface comprising the polymer preferably is nonchemically (covalently or noncovalently) connected to a layer or surface consisting of a metal or a metal alloy. The polymer layer or surface may be connected by an adhesive to the metal or metal alloy layer or surface.

Local administration of FK506 in accordance with the principles of the present invention is achieved by direct delivery from the active agent-loaded surface of the coronary or peripheral stent. An active agent-loaded surface of a stent may be obtained using any of a number of technological approaches. Each of these approaches is performed so that the active agent is released from the surface either over a short (hours) or an extended period (days). The kinetics of release also may be adjusted by carrying out specific modifications on the surface, e.g. by providing hydrophobic or hydrophilic side chains on a polymeric carrier or a ceramic surface. These surfaces also may be modified, e.g. by Si groups on an aluminum oxide layer.

The kinetics of release also may be adjusted by employing specific polymers, block polymers, polymer blends, graft polymers alone or in a layer structure. The kinetics of release are controlled particularly suitably by using microparticles, nanocapsules and/or liposomes and the polymer combinations described above. Nanoencapsulated active agents thus may be employed with prolonged activity. Liposomes are generally formed from phospholipids by dispersion in aqueous media and may be suitable because hydrophilic active agents may be incorporated into the aqueous internal volume and into the aqueous intermediate layers and hydrophobic active agents into the lipid layers. If nanocapsules and/or liposomes of different composition are used, the latter may be loaded with different active agents and thus a combination of active agents may be released in a targeted manner.

In another very favorable embodiment of the implant of the invention, the implant may be produced by a process in which FK506 is dissolved in the polymerization material before the formation of at least one closed or perforated layer or surface consisting of a polymer, or of a polymeric coating of the implant.

It is further particularly preferred for FK506 to be released after implantation of the implant of the invention. It is moreover particularly favorable for the release to be delayed. In this connection it is a particularly preferred embodiment of the invention for FK506 to be released from the implant over a period of 24 hr, preferably 48 hr, and more particularly more than 96 hr, after implantation. Alternatively, the FK506 may be released over at least 2 and up to 21 days after implantation. As a further alternative, the implant may show a first stage of release within 48 hours, and a second stage of release between 2 and 21 days after implantation.

The latter two-stage release variant in particular may be achieved by using two different types of coating, binding or physical immobilization. For example, a stent having laser-cut recesses loaded with FK506 may have the recesses sealed with an FK506-loaded biodegradable membrane. Rapid release from the membrane then is followed by long-term release from the recesses. Furthermore it is possible to use a base coat comprising a mixture of active agent and polymer and a top-coat comprising additional active agent or mixture thereof.

The present invention further relates to the use of an implant of the invention comprising FK506 for the treatment or prophylaxis of coronary or peripheral vascular constrictions or occlusions, in particular of constrictions or stenoses or restenoses, preferably for the prophylaxis of restenosis. Such an implant may comprise a stent, a stent graft, a graft, a graft connector, a guide wire, a catheter or a catheter pump as defined hereinabove. Preferably, the FK506 is bound or attached to the implant in such a way that it is released in a delayed manner after implantation.

In accordance with another aspect of the present invention, the implant of the present invention may comprise a polymer layer having, in a chemically covalently bound, noncovalently bound or physically immobilized form, at least one physiologically and/or pharmaceutically active active agent.

It is preferred that the active agent be selected from pharmaceutically active agents such as, for example, immunosuppressants or antibiotics, is preferably selected from the following active agents and derivatives thereof:

(Group 1:) molsidomine, linsidomine, sodium nitroprusside, nitroglycerin or general NO donors; stimulators of soluble guanylate cyclase (sGC), for example BAY 41-2272 (5-(cyclopropyl-2-[1-fluorobenzyl)-1H-pyrazolo[3,4-n]pyridin-3-yl]-pyrimidin-4-ylamine); hydralazine, verapamil, diltiazem, nifedipine, nimodipine or other $Ca^{2+}$channel blockers; captopril, enalapril, lisinopril, quinapril or other inhibitors of angiotensin converting enzymes (angiotensin converting enzyme inhibitors); losartan, candesartan, irbesartan, valsartan or other antagonists of the angiotensin II receptor;

(Group 2:) dexamethasone, betamethasone, prednisone or corticosteriods; FK 506 (tacrolimus) 17-beta-estradiol; cyclosporin; mycophenolic acid; VEGF, VEGF receptor activators; tranilast; meloxicam, celebrex, vioxx or other COX-2 antagonists; indomethacin, diclofenac, ibuprofen, naproxen or other COX-1 inhibitors; inhibitors of plasminogen activator-1 (plasminogen activator inhibitors-1) or serpins; thrombin inhibitors, for example hirudin, hirulog, agratroban, PPACK; interleukin-10;

(Group 3:) sirolimus, rapamycin, SDZ RAD (40-O-(2-hydroxyethyl) rapamycin or other rapamycin derivatives; PDGF antagonists; paclitaxel or 7-hexanoyl-taxol; cisplatin; vinblastine; mitoxantrone; combretastatin A4; topotecan; methotrexate; flavopiridol; actinomycin D; Rheopro/abciximab or probucol.

More particularly, the active agent is selected from:

(Group 1:) molsidomine, linsidomine, sodium nitroprusside, nitroglycerin or general NO donors; stimulators of soluble guanylate cyclase (sGC), for example BAY 41-2272 (5-(cyclopropyl-2-[1-(2-fluorobenzyl)-1H-pyrazolo[3,4-n ]pyridin-3-yl]pyrimidin-4-ylamine); captopril, enalapril, lisinopril, quinapril or other inhibitors of angiotensin converting enzymes (angiotensin converting enzyme inhibitors); losartan, candesartan, irbesartan, valsartan or other antagonists of the angiotensin II receptor;

(Group 2:) dexamethasone, betamethasone, prednisone or corticosteriods; FK506 (tacrolimus); VEGF, VEGF receptor activators; inhibitors of plasminogen activator 1 (plasminogen activator inhibitors-1) or serpins; and (Group 3:) sirolimus, rapamycin, SDZ RAD (40-O-(2-hydroxyethyl) rapamycin or other rapamycin derivatives; PDGF-antagonists; paclitaxel or 7-hexanoyl-taxol; mitoxantrone; combretastatin A4; flavopiridol.

Still more preferably, the implant comprises at least two or three physiologically and/or pharmaceutically active agents selected from one of groups 1 to 3, most preferably a maximum of one active agent selected from one group. Preferably, where an active agent is selected from aforementioned group 1, this active agent is released from the implant within the first 24-72 hr after implantation. If the active agent is selected from aforementioned group 2, this active agent is released from the implant within the first 48 hr-21 days after implantation. If the active agent is selected from aforementioned group 3, this active agent is released from the implant within 14 days to 3 months after implantation.

Preferred modes of providing medical implants comprising FK506, alone or with another active agent as described hereinafter, are now described. Such implants include:

(a) implants having FK506 directly deposited on the exterior surface of the implant;

(b) implants having FK506 loaded into recesses formed in an exterior surface of the implant;

(c) implants having FK506 loaded into voids or pores of a ceramic coating disposed on the exterior surface of the implant;

(d) implants having FK506 loaded into an interior reservoir of an implant that communicates with an exterior of the implant via one or more passageways;

(e) implants having FK506 applied in a resinous form to a delivery system used to deploy the implant;

(f) implants having FK506 bound to a polymeric coating applied to an exterior surface of the implant; and (g) implants having FK506 chemically bound to a polymeric layer that covers a portion of the exterior surface of the implant.

Each of these modes, and exemplary methods of making implants using such modes, are now described.

(a) Implants Having FK506 Directly Deposited on the Exterior Surface of the Implant In accordance with one aspect of the present invention, a medical implant, such as a stent formed from a slotted metal alloy tube, may have a coating of FK506 applied directly to the exterior surface of the stent. In particular, FK506 in its as-manufactured state as a relatively high viscosity liquid, may be thinned slightly and applied to the exterior of a stent by brush, spray or dipping. The stent is then allowed to air dry. Upon deployment in a patient's vessel, the FK506 will be placed into intimate contact with the vessel lining, where it will be locally absorbed by the vessel wall. Implants of other types, including without limitation stent-grafts, grafts and graft connectors, may be prepared by a similar method.

(b) Implants Having FK506 Loaded into Recesses Formed in an Exterior Surface of the Implant As a variation of the embodiments described by direct application of FK506 to the exterior surface of the implant, the implant may be formed or processed by a suitable surface finishing technique, e.g., sand blasting, etching or laser cutting, to form recesses on the exterior surfaces of the implant. For example, recesses may be formed in the exterior surfaces of the struts of a slotted-tube stent using a laser. The recesses then are filled with FK506. Alternatively, the recesses of the implant may be filled with FK506 that is bound to a polymeric coating, or a polymeric material in which FK506 has been dissolved before polymerization of the coating.

As further option, a polymeric biodegradable coating may be applied to the recess-filled implant, wherein the coating also is loaded with an active agent, e.g., FK506 or any of the other active agents discussed hereinabove. After an initial release from the polymeric coating, active agent can be released long-term from the active agent-filled recesses. This technical approach corresponds in the other details to those already described above.

(c) Implants Having FK506 Loaded into Voids or Pores of a Ceramic Surface Coating A further variation in the surface treatment of an implant of the present invention may comprise a coating of porous ceramic to the exterior of the implant. The pores of the ceramic are then filled with FK506 and serve as reservoirs that subsequently release the FK506 after implantation. An addition amount of FK-506 also may be deposited on top of the ceramic. An aluminum oxide coating suitable for this purpose is described in German patent applications DE 19855421, DE 19910188 and International Application WO 00/25841. It is moreover possible to employ other types of metal oxide coatings, such as the iridium oxide coating described in U.S. Pat. No. 6,245,104 B1. Accordingly, every mention of aluminum oxide hereinafter should be understood to include other metal oxides such as, for example, iridium oxide.

The porous surface of the ceramic coating may be loaded with FK506 in amounts between 10 µg and 10 mg either by immersing, spraying on or a comparable technique. The dose of active agent depends on the type of target vessel and the condition of the patient and is chosen so that proliferation, migration and T-cell response are adequately inhibited without impeding the healing process. FK506 may be used as aqueous or organic solution, for example in DMSO, DMF and ethanol. After the spraying or immersing (optionally under weak vacuum), the treated stent is dried and the procedure is repeated 2-10 times.

Alternatively, the FK506 and/or other active agent may be directly applied onto the exterior of the implant with the aid of a micropipette or of a robotic pipettor. After the last drying step, the implant may be rinsed in water or isotonic saline at room temperature for one minute and then redried. The active agent content can be analyzed by standard methods (HPLC, LC-MS) after the active agent has been dissolved out with a suitable solvent, with the kinetics of release measured using a standard release-measuring apparatus. Optionally, a biodegradable polymeric coating may be applied over the FK506-filled ceramic coating to provide multi-staged release.

(d) Implants Having FK506 Loaded into an Interior Reservoir of an Implant that Communicates With an Exterior of the Implant Via One or More Passageways As an alternative to the porosity of a ceramic coating, which serve as microscopic reservoirs is described, an implant may instead comprise one or more macroscopic reservoirs that communicate with the exterior surface of the implant via one or more passageways or channels. The reservoirs are then loaded with FK506, alone or in combination with other active agents, as discussed hereinabove, so that the FK506 and other active agents may be released from the reservoir to the exterior surface of the implant following implantation.

Referring to FIG. 1, exemplary stent 10 is described that may be formed by welding together individual sinusoidal rings of tubular wire 12 at joints 13, wherein each wire 14 includes internal lumen 16. A plurality of passageways 18 or channels may be cut, e.g., by laser, extending inward from exterior surface 20 of stent 10, so that passageways 18 communicate with internal lumen 16. Once the stent structure is complete, FK506 and/or other active agents may be loaded into the reservoir. Optionally, the FK506 may be dissolved within a polymeric material that is subsequently polymerized after loading into the reservoirs of the implant. As a further option, the exterior surface of the stent may itself be coated with a biodegradable polymer containing FK506 or other active agent to provide multi-stage release.

(e) Implants Having FK506 Applied in a Resinous Form to a Delivery System

As yet another alternative, FK506 in its as-manufactured form has a high viscosity, resinous form that advantageously may be used to adhere an implant to the implant delivery system. For example, U.S. Pat. No. 6,488,702 to Besselink describes a stent comprising a plurality of bi-stable spring cells that is mounted for delivery on a balloon catheter. A resinous form of FK506 may be applied to the balloon-mounted stent to assist in retaining the stent on the balloon during delivery. Likewise, a resinous form of FK506 may be applied to grafts, stent-grafts or other implants to adhere the implant to an implant delivery system, thus achieving dual objectives of facilitating anchoring of the implant to the delivery system and reducing the risk of post-deployment restenosis.

(f) Implants Having FK506 Bound to a Polymeric Coating Applied to an Exterior Surface In other embodiments of the implant of the present invention, a polymeric coating is disposed on the implant to which FK506 is physically or chemically bound. Preferred polymeric coatings include methacrylate polymers, polyurethane, PTFE, hydrogel or hydrogel/polyurethane blends. Alternatively, FK506 may be dissolved in the polymerization material before the formation of at least one closed or perforated layer or surface consisting of a polymer, or of a polymeric coating of the implant.

Polymers are suitable for active agent loading: methacrylate polymers, polyurethane coatings, PTFE coatings, hydrogel coatings. The FK506 and, optionally, other active agent(s) selected from those listed above, either may be applied to the final surface, e.g., by brush, dipping or spray as described hereinabove, or may be added directly to the polymerization solution.

In addition, polymers and combinations of the latter in the form of polymer blends, systems with a layer structure, block copolymers, graft copolymers may be used, including: acrylates and methacrylates, polyphosphazenes, silicones such as, for example, polydimethylsiloxane, polymethylenemalonic esters, polyethers, polyesters, bioabsorbable polymers, polymers from vinylic monomers such as, for example, polyvinylpyrrolidone and vinyl ethers, poly-cis-1,4-butadiene, poly-cis-1,4-isoprene, poly-trans-1,4-isoprene, and vulcanized products, polyurethanes, polyureas, polyamides, polyimides, polysulfones, and biopolymers such as, for example, cellulose and derivatives thereof and proteins and fibrin glues. Of particular interest are hydrogels that display, because of their high water uptake, very good hemocompatibility as an outermost layer (top coat).

It also is possible to employ hydrogels such as, for example, polyacrylamide, polyacrylic acid, polymers with oxygen as heteroatom in the main chain such as, for example, polyethylene oxide, polypropylene oxide, polytetrahydrofuran. The FK506 or other active agent either may be applied to the final surface of the implant or administered embedded in nanocapsules and/or liposomes. The active agent may, however, also be present directly in the polymerization solution or in the polymer solution. It is possible with some polymer/active agent systems for the active agent to be immobilized by swelling.

(g) Implants Having FK506 Bound to a Polymeric Layer

In a further alternative embodiment, the implant may comprise a separate polymeric layer material that is applied to an implant. The polymeric layer may be separately polymerized as a sheet or layer, and then attached to a metal, metal alloy or polymer substrate to form the implant.

Figure 2:
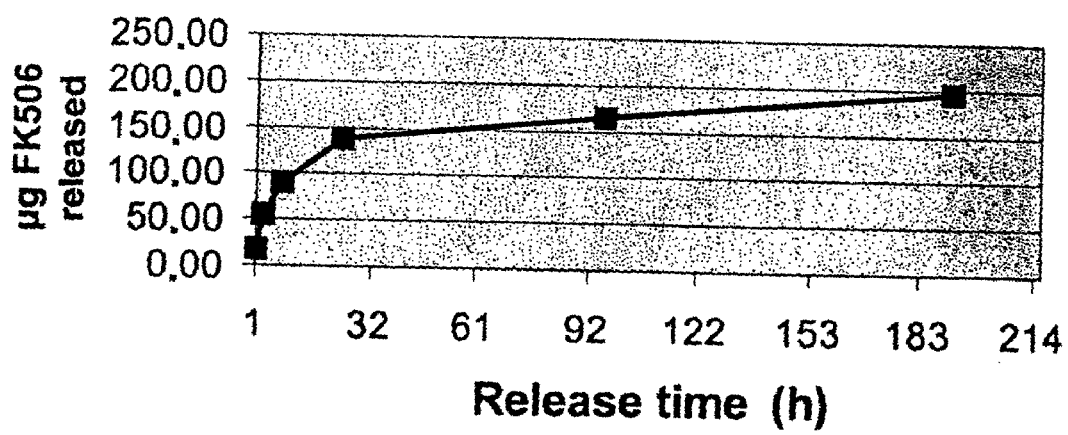
FIG. 2 is a graph showing release of FK506 from a PTFE coronary stent graft having its surface loaded with FK506.

For example, a stent-graft as described in U.S. Pat. No. 5,916,264 to Von Oepen et al. comprises a layer of polymeric graft material, such as PTFE, captured between slotted tubular stents. Advantageously, FK506 may be applied to the surface of the polymeric graft material before it is incorporated into the stent graft. Alternatively, the FK506 may be dissolved into the polymerization material used to form a coating on the graft material. FIG. 2 shows the release of FK506 from a coronary stent graft in which the PTFE surface has been loaded with FK506.

As yet another example, a polymeric layer containing FK506 may be applied over the exterior of a metal alloy stent having FK506-filled recesses, thereby providing multi-stage release. For example, FK506 may be deposited in the recesses of porous PTFE membrane, and the membrane then used as an exterior cover for a stent, graft, stent-graft, graft connector or other medical implant. Other variants of the foregoing techniques will be apparent to one of ordinary skill in the design of implants.

As a further example, one or more polymers may be dissolved in a solvent or a solvent system and one or more active agents added to the solution in a defined manner. The solution is sprayed on the implant and the solvent is permitted to evaporate. The active-agent laden polymer film deposited on the implant causes a sustained of the embedded active agent or mixture of active agents.

Methods of Making the Implants of the Present Invention

In accordance with another aspect of the present invention, methods of making implants containing FK506, alone or in combination with other active agents, are now described.

A first exemplary method of making an implant in accordance with the present invention is now described for a stent comprising at least one closed or perforated layer or surface formed from homogenous metal or a metal alloy material or strands, wherein the stent is coated with a ceramic coating, e.g., of aluminum oxide. The ceramic-coated stent preferably is brought into contact with an FK506 solution in aqueous or organic solvent, for example by sprinkling, spraying or immersing, optionally under vacuum. Optionally, the implant may then be dried, preferably until the solvent is removed. The steps of applying the FK506 solution to the stent followed by drying may be repeated, preferably several times, and more preferably 1 to 5 times. The stent then optionally is rinsed one or more times with water or isotonic saline and again, optionally, subsequently dried and packaged for use.

In the foregoing method, the FK506 solution preferably is prepared by dissolving FK506 in alcohol, preferably in ethanol, in a concentration of 0.5-5 g/l. Alternatively, instead of several applications of FK506 solution to the stent, as described above, it may be preferable that the stent be brought into contact with the FK506 solution in aqueous or organic solvent by immersing the stent in the FK506 solution under vacuum for several hours, e.g., preferably overnight, followed by washing the stent several times with saline and drying the stent overnight.

As a further alternative, the stent may be produced having a ceramic coating, and without application of FK506, and then be packaged, preferably sterilely, into a preferably sterile vessel with a closure that may be resealably perforated. For example, the stent may be packaged in a glass vial having a self-sealing membrane closure. FK506 solution then may be sterilely introduced into the vessel.

A thin, preferably sterile, air-pervious ventilation tube, for example a cannula, may then be inserted into the vial through the resealable closure to permit a vacuum to be applied to outgas the ceramic coating of the stent. Preferably, the FK506 solution may be agitated, and after a predetermined period has elapsed, e.g., 12 hr, the ventilation tube may be removed. The stent remains in the vial until used. Preferably, the FK506 solution is formed by dissolving FK506 in alcohol, preferably ethanol, in a concentration of 3.3 mg of FK506 in 1 ml of ethanol.

The foregoing alternative is particularly advantageous both with respect to cost, manufacturing time, and product shelf-life, since the implant may be activated with FK506 in the field shortly before use and is already in a sterile packaging. Advantageously, this method of the present invention is not confined for use with FK506, but is expected to function well with a large number of other active agents, such as those described hereinabove.

The foregoing methods illustratively are described with respect to a ceramic coated stent, but are equally well suited for other types of implant of the present invention, including: implant comprising a polymer rather then metal or metal-alloy stent; implants coated with a coating that is polymerized or polymerizing on the surface; implants having internal reservoirs communicating with an exterior surface via passageways; implants having polymer layers; and implants having exterior surfaces with FK-506 filled recesses, and optionally, a biodegradable polymer coating.

EXAMPLES

Example 1

Loading of Selected Active Agents onto Stent Grafts
All values are stated in µg.

TABLE 1

| Active agent/ type of stent | FK 506 (tacrolimus) | Vinblastine | Paclitaxel (Taxol) | Cisplatin | Mito-xantrone |
|---|---|---|---|---|---|
| A | 1382 | 4 | 128 | 15* | 116 |
|   | 1671 | 125 | 155 | 14* | 142 |
|   | 1625 | 238 | 148 | 14* | 113 |
| Average | 1559 | 146 | 144 | 14 | 124 |
| B |  | 18 |  |  |  |
|   |  | 16 |  |  |  |
|   |  | 21 |  |  |  |
| Average |  | 18 |  |  |  |
| C |  | 194 |  |  |  |
|   |  | 165 |  |  |  |
| Average |  | 180 |  |  |  |

*measured by AAS
A: Experiments with dissolved solids in which stent grafts with a PTFE polymer layer were immersed in the solution.
B: Experiments with i.v. solutions in which stent grafts with a PTFE polymer layer were immersed in the solution.
C: Experiments with i.v. solutions in which polyurethane-coated stents were immersed in the solution.

Example 2

Release Patterns of Various Stent Grafts and Stents Having Polymeric Coating of the Present Invention
All values are stated in µg.

To analyze the active agent release, a stent was incubated at 37° C. in 10 ml of PBS buffer (stabilized with Na azide) at 37° C. After defined periods of time had elapsed, 2×1 ml of the solution were removed and analyzed. These 2 ml were replaced by fresh PBS buffer (stabilized with Na azide).

The tables reflect the total released content of active agent in the solution., ie., the amounts of active agent in the buffer volume removed for the analysis are accumulated with amounts detected in subsequent examples.

TABLE 2

| | Vinblastine | | | | |
|---|---|---|---|---|---|
| Active agent/ Type | after 1 hr | after 3 hr | after 8 hr | after 24 hr | after 96 hr after 72 hr |
| A | 73 and 75 | 108 and 114 | 121 and 126 | 106 and 120 | 132 and 140 |
|   | Average: 74 | Average: 109 | Average: 124 | Average: 113 | (96 hr) Average: 136 |
|   | 37 and 41 | 48 and 51 | 47 and 58 | 57 and 62 | 56 and 57 |
|   | Average: 39 | Average: 50 | Average: 42 | Average: 60 | (72 hr) Average: 57 |
|   | 80 and 86 | 99 and 104 | 108 and 117 | 117 and 127 | 113 and 121 |
|   | Average: 83 | Average: 102 | Average: 113 | Average: 122 | (72 hr) Average: 117 |

A: Experiments with dissolved solids in which stent grafts with a PTFE polymer layer were immersed in the solution.

TABLE 3

| Active agent/ type | | | FK 506 (tacrolimus) | | | |
|---|---|---|---|---|---|---|
|  | after 1 hr | after 3 hr | after 8 hr | after 24 hr | after 96 hr | after 192 hr |
| A 1st stent | 14 and 13 Average: 14 | 62 and 62 Average: 62 | 92 and 99 Average: 95 | 148 and 145 Average: 147 | 145 and 151 Average: 148 | 195 and 198 Average: 196 |
| A 2nd stent | 34 and 26 Average: 30 | 56 and 57 Average: 57 | 82 and 78 Average: 80 | 108 and 109 Average: 109 | 159 and 164 Average: 161 | |
| A 3rd stent | 12 and 9 Average: 11 | 47 and 43 Average: 45 | 101 and 93 Average: 95 | 154 and 155 Average: 154 | 184 and 190 Average: 187 | |

A: Experiments with dissolved solids in which stent grafts with a PTFE polymer layer were immersed in the solution.

TABLE 4

| Active agent/ type | | | FK 506 (tacrolimus) | | | | |
|---|---|---|---|---|---|---|---|
|  | after 1 hr | after 3 hr | after 8 hr | after 24 hr | after 96 hr | after 264 hr | after 367 hr |
| C 1st stent | 19 and 20 Average: 20 | 25 and 26 Average: 26 | 33 and 33 Average: 33 | 41 and 39 Average: 40 | 43 and 38 Average: 41 | | |

TABLE 4-continued

FK 506 (tacrolimus)

| Active agent/ type | after 1 hr | after 3 hr | after 8 hr | after 24 hr | after 96 hr | after 264 hr | after 367 hr |
|---|---|---|---|---|---|---|---|
| | after 1 hr | after 3 hr | after 8 hr | after 24 hr | after 96 hr | | |
| C 2nd stent | 20 and 27 Average: 24 | 21 and 24 Average: 22 | 26 and 30 Average: 28 | 34 and 31 Average: 32 | 37 and 35 Average: 36 | 85 | 88 and 94 Average: 91 |

C: Experiments with i.v. solutions in which polyurethane-coated stents were immersed in the solution.

TABLE 5

| | Paclitaxel | | | | | |
|---|---|---|---|---|---|---|
| Active agent/ Type | after 1 hr | after 3 hr | after 8 hr | after 24 hr | after 96 hr | after 192 hr |
| A | 0.14 and 0.23 Average: 0.19 | 0.46 and 0.53 Average: 0.50 | 1.42 and 1.25 Average: 1.34 | 1.65 and 1.42 Average: 1.54 | 1.42 and 1.93 Average: 1.68 | 2.22 and 2.24 Average: 2.23 |
| | 0.42 and 0.52 Average: 0.47 | 0.90 and 0.90 Average: 0.90 | 1.16 and 1.21 Average: 1.19 | 2.44 and 2.40 Average: 2.42 | 2.79 and 2.78 Average: 2.79 | |
| | 0.20 and 0.16 Average: 0.18 | 0.51 and 0.95 Average: 0.73 | 0.89 and 0.94 Average: 0.92 | 2.26 and 2.27 Average: 2.27 | 2.82 and 2.82 Average: 2.82 | |

A: Experiments with dissolved solids in which stent grafts with a PTFE polymer layer were immersed in the solution.

TABLE 6

| Active agent/ Type | Cisplatin | | | |
|---|---|---|---|---|
| | after 1 hr | after 3 hr | after 8 hr | after 24 hr |
| A | 11.7 and 11.9 Average: 11.8 | 15.4 and 15.4 Average: 15.4 | 16.3 and 16.5 Average: 16.4 | 16.1 and 15.9 Average: 16.0 |
| | 5.7 and 5.4 Average: 5.5 | 7.8 and 7.7 Average: 7.8 | 9.9 and 9.8 Average: 9.8 | 10.9 and 11.1 Average: 11.0 |
| | 10.0 and 10.0 Average: 10.0 | 11.4 and 11.8 Average: 11.6 | 12.2 and 12.3 Average: 12.2 | 12.4 and 12.2 Average: 12.3 |

A: Experiments with dissolved solids in which stent grafts with a PTFE polymer layer were immersed in the solution.

TABLE 7

| Active agent/ Type | Mitoxantrone | | | |
|---|---|---|---|---|
| | after 1 hr | after 3 hr | after 8 hr | after 24 hr |
| A | 57 and 86 Average: 71 | 55 and 52 Average: 54 | 49 and 47 Average: 48 | 42 and 49 Average: 45 |
| | 70 and 74 Average: 72 | 80 and 83 Average: 81 | 80 and 82 Average: 81 | 72 and 75 Average: 74 |
| | 29 and 27 Average: 28 | 25 and 27 Average: 26 | 23 and 21 Average: 22 | 24 and 29 Average: 27 |

A: Experiments with dissolved solids in which stent grafts with a PTFE polymer layer were immersed in the solution.

Example 3

Production Process (1) for FK506-coated Stents
  10 mg of FK506 are dissolved in 3 ml of ethanol.
  Uncoated stainless steel stents are immersed in the solution at room temperature under vacuum overnight.
  Wash three times with saline for 1 minute.
  Dry overnight.

Example 4

Production Process (2) for FK506-coated Stent Grafts
  The dosage of FK506 may vary according to the stent length and diameter and according to the intended use in the body. A dosage of 10-200 µg of FK506 per cm of stent length was used in this case. FK506 is dissolved (appropriate for the desired dosage) in ethanol in a small glass vessel, and the solution is examined visually for crystals.
  Unpretreated stent grafts ("JOSTENT Coronary Stent Graft") comprising a sandwich construction of two stainless steel stents with a PTFE membrane are mounted on holders.
  A pipette is used to deposit a selected amount of FK506 solution (5 to 30 µl) onto the mounted stent graft.
  Application of FK506 solution is repeated as desired to achieve larger concentrations of FK506 on the implant. In the present case, the procedure was repeated once.
  After FK506 deposition is complete, the stent graft is removed from the holder.
  After brief drying in air (about 5 min), optionally with input of heat, the stents may be packaged.
  All stents are examined under a lens for medicament flocculation; defective stent grafts are discarded.

Example 5

Production Process (3) for FK506-coated Stent Having a Ceramic Coating
  50 mg of FK506 are dissolved in 10 ml of ethanol in a glass vessel. All further concentrations are prepared from this stock solution, as required, by dilution (dilutions between 1:1 and 1:20).
  The solution is examined visually for crystals.
  Unloaded stents coated with an aluminum oxide layer, as described above, are mounted on holders.
  A hypodermic syringe is used to apply the FK506 solution (5 to 50 µl) dropwise to the stent, with the solution being distributed evenly over the stent.
  The loaded stent is removed from the holder.
  After brief drying in air (about 5 min), optionally with input of heat, the stents may be packaged.

All stents are examined under a lens for medicament flocculation; defective stents are discarded.

Example 6

Production Process (4) for FK506 and Other Active Agents, to Produce Sterile Implants Small injection vials that are not much larger than the implant are used.

Sterile implants are placed sterilely in the sterile injection vial.

0.5 ml of sterile-filtered FK506 solution (3.3 mg/ml in ethanol) are added to the vials.

The vials are closed with rubber stoppers.

Each rubber stopper is pierced with a sterile injection cannula with sterile filter.

The vials are placed horizontally on a roller apparatus under vacuum in a desiccator.

The vials are rolled under vacuum overnight.

The injection cannula is removed.

No rinsing is carried out.

The sterile implants are ready for use.

Example 7

A Selection of Possible Active Agents for an Active Agent-releasing Implant Having a Plurality of Layers The listed active agents are classified into groups 1-3 according to their preferred release profile or the release time period. The listed active agents also include derivatives and all types of salts, enantiomers, racemates, bases or free acids.

Of particular interest here are stents, stent grafts and polymeric surface stents which comprise and correspondingly release at least one, two or three of the active agents listed below. It is moreover preferred for the stents, stent grafts and polymeric surface stents to comprise active agents from different groups.

TABLE 8

Phase I - Vasodilation (group 1)
Active agents that are released during the first 24-72 hr after implantation.

| Active agent |
| --- |
| molsidomine, linsidomine, sodium nitroprusside, nitroglycerin, NO donors in general |
| stimulators of soluble guanylate cyclase such as BAY 41-2272 (5-(cyclopropyl-2-[1-(2-fluorobenzyl)-1H-pyrazolo[3,4-n]pyridin-3-yl]pyrimidin-4-ylamine |
| Hydralazine |
| verapamil, diltiazem, nifedipine, nimodipines and other $Ca^{2+}$ channel blockers |
| captopril, enalapril, lisinopril, quinapril and other inhibitors of angiotensin converting enzymes |
| losartan, candesartan, irbesartan, valsartan and other angiotensin II receptor antagonists |
| α - blockers |

TABLE 9

Phase II - Inhibition of inflammation, immunosuppression, promotion of cell growth of endothelial cells, inhibition of cell migration (group 2)
Active agents that are released during the first 2-21 days after implantation.

| Active agent |
| --- |
| dexamethasone, betamethasone, prednisone and other corticosteriods |
| 17-beta-estradiol |
| FK506 (tacrolimus) |
| Cyclosporin |
| mycophenolic acid |
| VEGF, VEGF receptor activators |
| Tranilast |
| meloxicam, celebrex, vioxx and other COX-2 antagonists |
| indomethacin, diclofenac, ibuprofen, naproxen and other COX-1 inhibitors |
| plasminogen activator inhibitor 1 and other serpins |
| thrombin inhibitors such as hirudin, hirulog, agratroban, PPACK etc. |
| interleukin-10 |

TABLE 10

Phase III - Inhibition of cellular proliferation (group 3)
Active agents that are released within the first 14 days to 3 months after implantation

| Active agent |
| --- |
| sirolimus, SDZ RAD (40-O-(2-hydroxyethyl)-rapamycin and other rapamycin derivatives |
| PDGF antagonists |
| Paclitaxel |
| Cisplatin |
| Vinblastine |
| Mitoxantrones |
| combretastatin A4 |
| Topotecan |
| methotrexate |
| flavopiridol |

Local administration of the active agent is achieved by direct delivery from the active agent-loaded surface of a coronary or peripheral stent. An active agent-loaded surface of a stent may be prepared using various methods described hereinabove. Each of these methods may be carried out so that the active agent is released from the surface either in a short (hours) or an extended period (days). The kinetics of release can be adapted by carrying out specific modifications on the surface, e.g. hydrophobic or hydrophilic side chains of a polymeric carrier or a ceramic surface.

Example 8

Figure 3A:
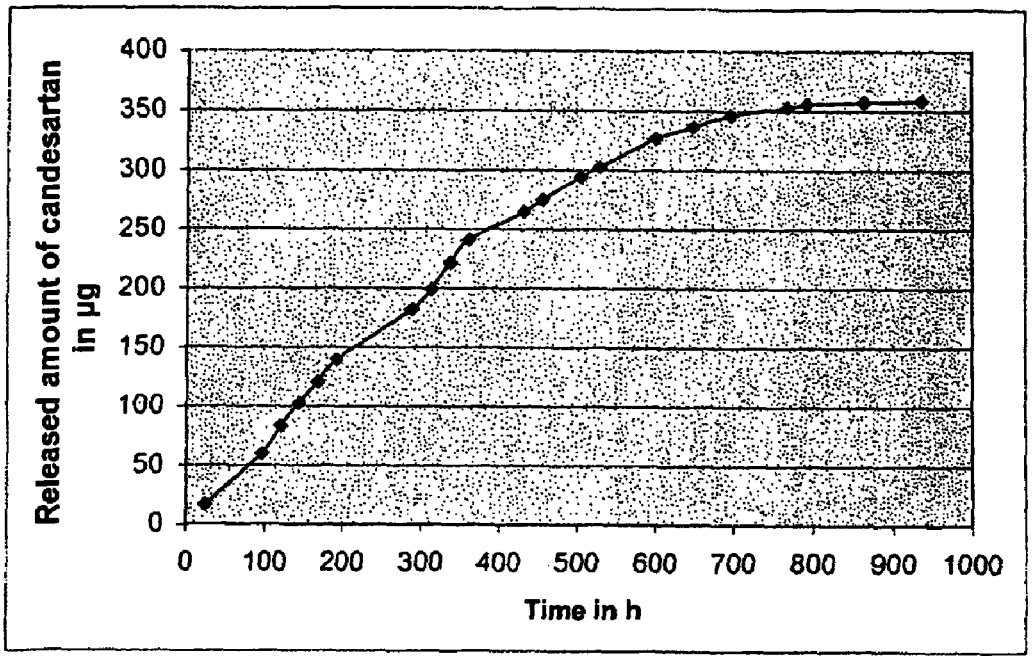
FIGS. 3A and 3B are, respectively, graphs showing the release of candesartan and quinapril from a PTFE stent graft having its surface coated with either candesartan or quinapril.
Figure 3B:
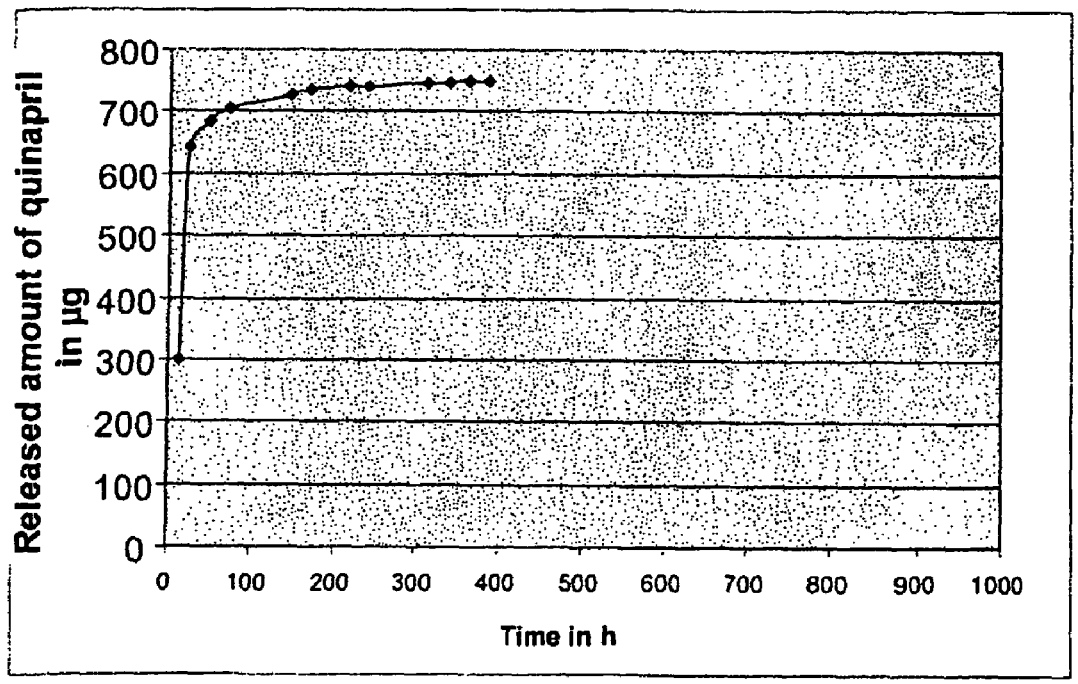
Figure 4A:
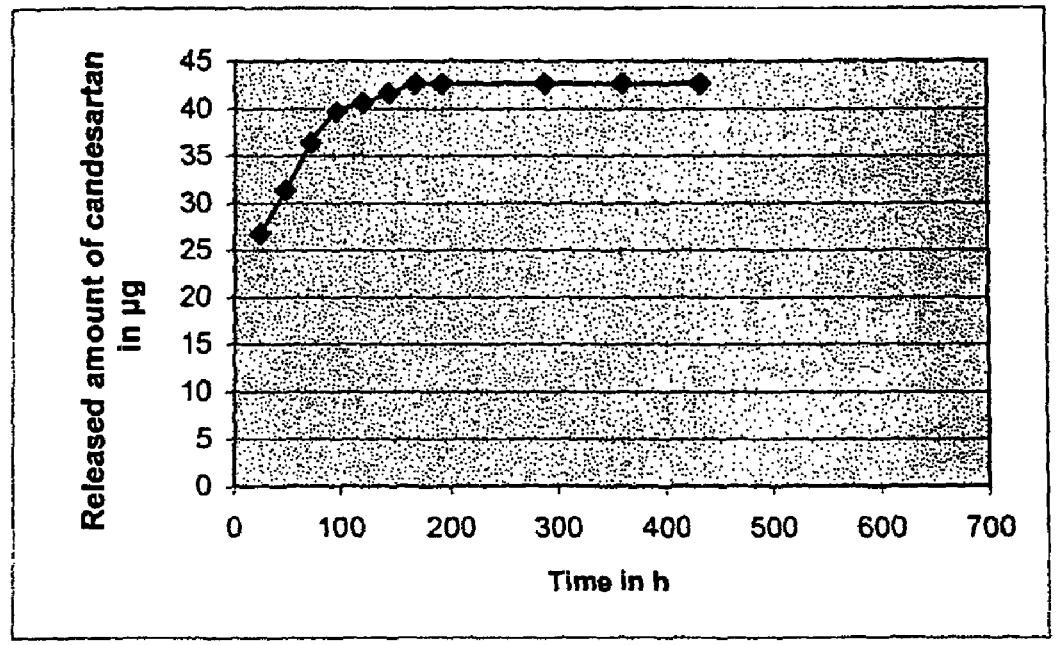
FIGS. 4A and 4B are, respectively, graphs showing release of candesartan and quinapril from a polyurethane-coated stent, wherein the coating has been supplemented with either candesartan or quinapril.
Figure 4B:
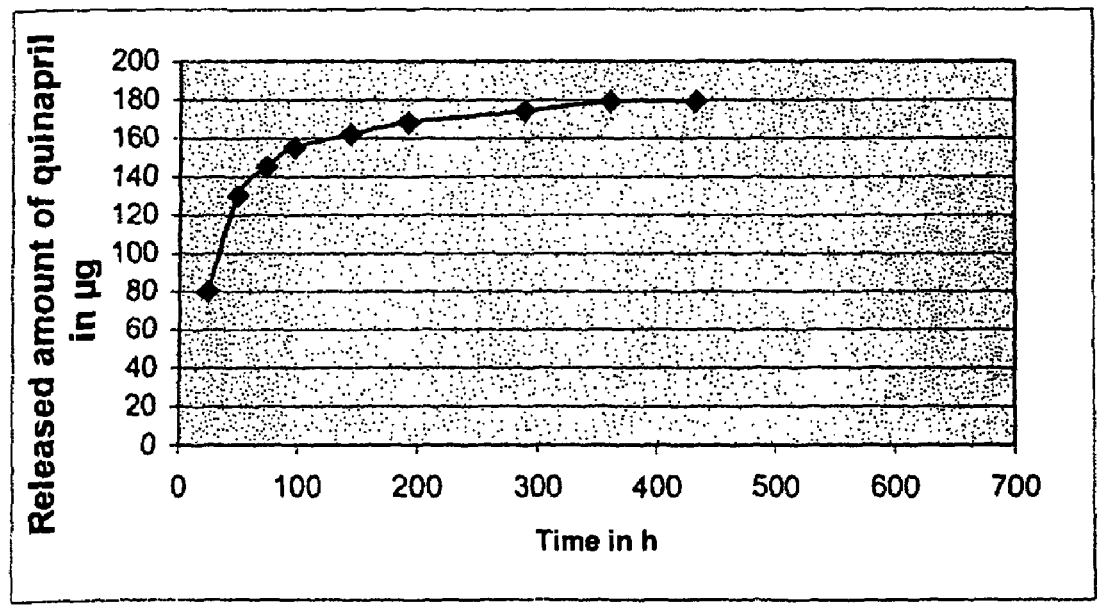

Active Agent Release of Candesartan and Quinapril From (Polymer-)coated Stents a) Stents were provided with a porous PTFE membrane. This membrane then was loaded with an active agent mixture of candesartan and quinapril (1 mg each). The two active agents are released simultaneously. The release was measured in PBS (phosphate buffered saline). FIGS. 3A and 3B show the active agent release of candesartan and quinapril, respectively, from the stent.

b) Open-cell stainless steel stents were provided with a polyurethane coating. An active agent mixture of candesartan and quinapril (15% each based on the polyurethane content) was introduced into a 5% solution of the polyurethane in dimethylacetamide and applied to the stent by a spraying process. FIGS. 4A and 4B show the corresponding active agent releases.

c) Open-cell stainless steel stents were provided with a polyurethane/hydrogel coating. An active agent mixture of candesartan and quinapril (15% each based on the polymer content) was introduced into a 5% solution of the polymer blend in dimethylacetamide and applied to the stent by a spraying process.

Figure 5A:
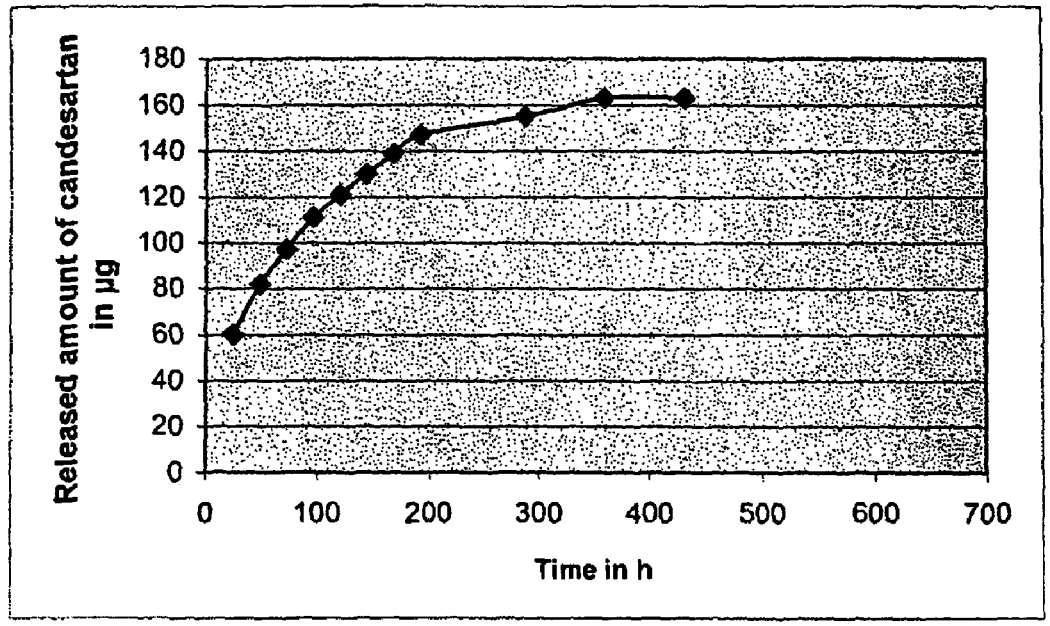
FIGS. 5A and 5B are, respectively, graphs showing release of candesartan and quinapril from a stent coated with a polyurethane/hydrogel blend, wherein the coating has been supplemented with either candesartan or quinapril.
Figure 5B:
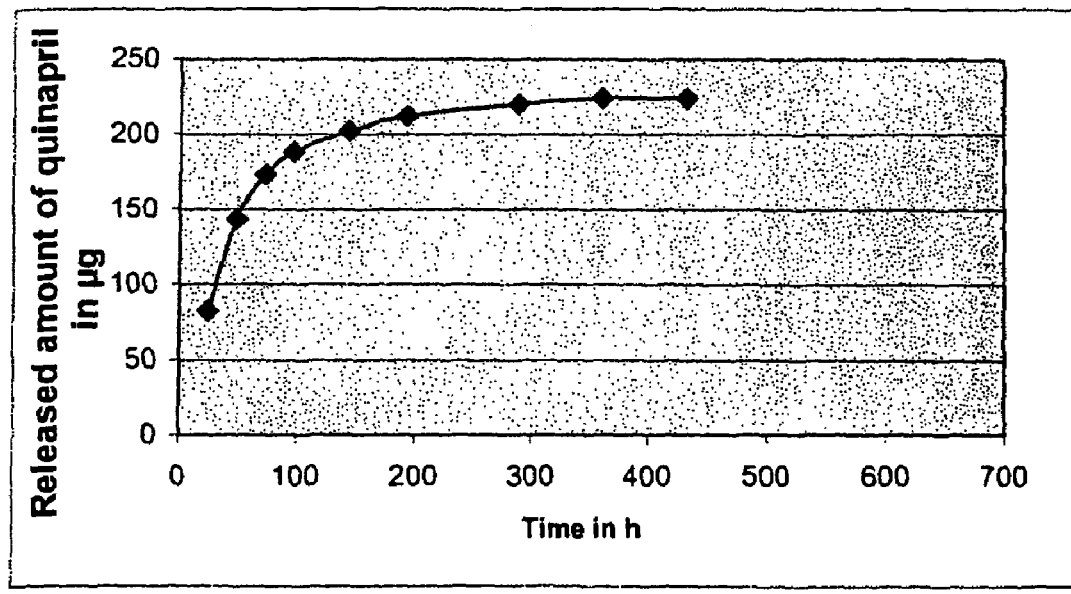

FIGS. 5A and 5B show the corresponding active agent releases.

Example 9

Animal Study of the Kinetics of Release and Mode of Action of FK506

Stainless steel coronary stents (JOSTENT Flex, 16 mm) were coated with an aluminum oxide ceramic layer. This coating served as carrier of FK506 (as described in Example 5). In this case, the stents were loaded with a total of 60 µg of FK506. In an animal study in rabbits (n=7), these FK506 coated stents and normal stents without coating were implanted into the carotid artery of New Zealand rabbits. The release of FK506 and the effect of FK506 on the growth of the intima and the formation of macrophages and lymphocytes was investigated.

Figure 6:
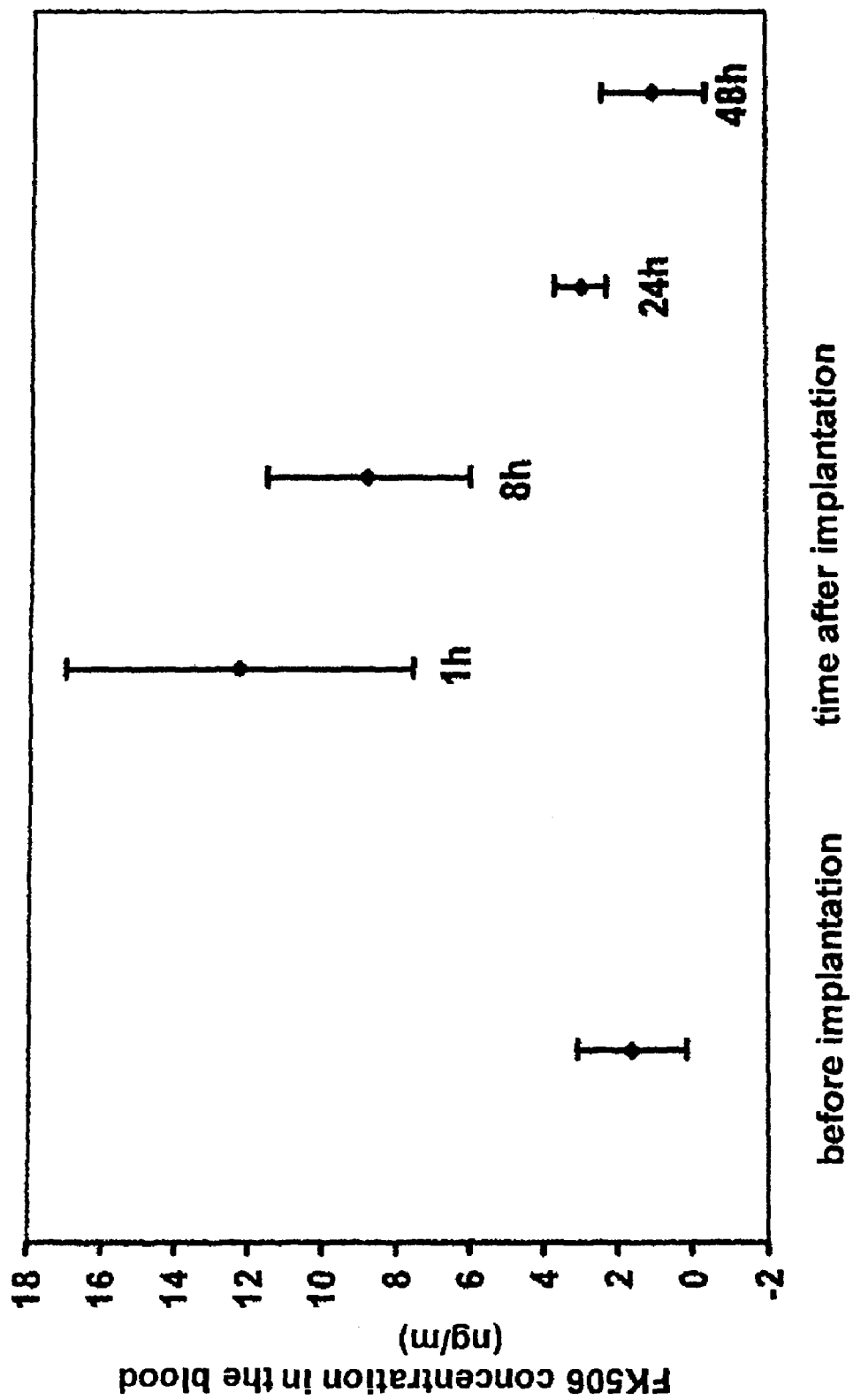
FIG. 6 is a graph showing release of FK506 in the blood after implantation of FK506-coated stents in rabbits.
Figure 7:
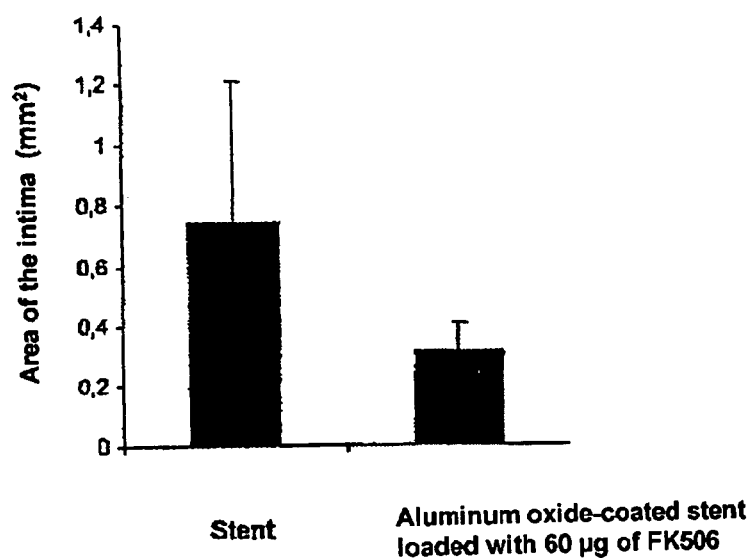
FIG. 7 is a graph showing the areas of the intima on implanted stents with and without a coating including FK506.
Figure 8:
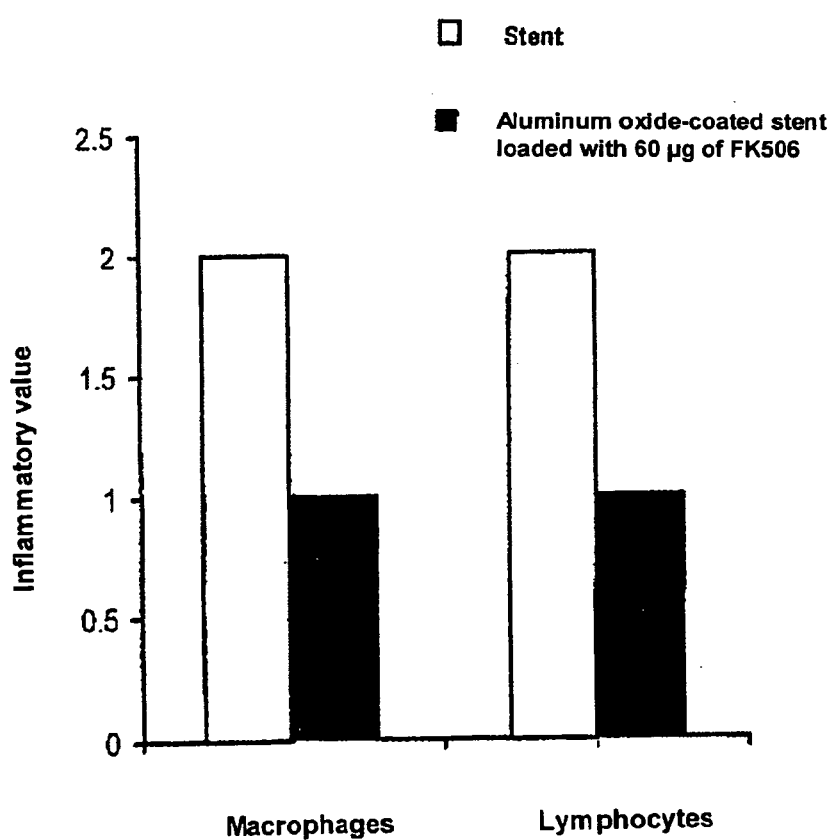
FIG. 8 is a graph showing the inflammatory reaction to implantation of stents with and without a coating including FK506.

The release of FK506 were determined by HPLC determination of the amount of FK506 in the blood of the rabbits after 1 hr, 8 hr, 24 hr and 48 hr. FIG. 6 is a graph showing the release of FK506 over time. The rabbits were sacrificed after 28 days, and the implanted stents were examined. The area of newly grown intima (neointima) within the stent was quantified under the optical microscope, and is reported in FIG. 7. There is a reduction of 53% in the formation of neointima for stents loaded with 60 µg of FK506 compared with bare stents. This reduction in neointima formation was accompanied by a detectable decrease in the foci of inflammation. The formation of macrophages and lymphocytes is shown in FIG. 8. The use of stents with a ceramic coating onto which FK506 is applied thus leads to a distinct reduction in neointima and in foci of inflammation after the implantation.

Example 10

Method of Spray Coating Implants with FK506

In accordance with another aspect of the present invention, a method of depositing drugs and polymers containing FK506 on implant surfaces employs a spray coating technique wherein the coating substrate is only present on the implant. The following spray method leads to coated implants, e.g., stents, which are then dipped in FK506 or other active agents to embed the drug. Advantageously, this method provides coated implants with reduced webbing and pooling of the polymer coating.

The coating solution is first prepared dissolving the polymer in a solvent yielding a concentration of 1-15% and more preferably 3-5%. Suitable polymers and blends thereof are described hereinabove and further include polyphosphazenes and hyaluronic acid-based polymers. Suitable solvents and mixtures thereof include N,N-dimethylacetamide, N,N-dimethylformamide, dimethylacetal, dimethylsulfoxide, sulfolane, N-methylpyrrolidone, tetrahydrofuran, acetonitrile, chlorbenzene, teraline, toluene, 1,1,2-trichloroethene, xylene, chloroform, dichloromethane, 1,4-dioxan, 2-ethoxyethanol, ethyleneglycol, hexane, heptane, pentane, 1-pentanol, 1-propanol, 2-propanol methanol, 2-methoxyethanol, methylbutyl ketone, methylcyclohexane, cyclohexane, 1,2-dichlorothene, nitromethane, acetic acid, formic acid, acetone, 1-butanol, 2-butanol, ethyl acetate, methyl acetate, ethyl ether, ethyl formate, ethanol, cumene, butyl acetate, propyl acetate, isobutyl acetate, isopropyl acetate tert-butylmethyl ether, anisole, 3-methyl-1-butanol, methylethyl ketone, methylisobutyl ketone, 2-methyl-1-propanol.

The coating solution is then placed in the glass vial of a pressurized spray vessel and a tube for the material flow, which is connected with the spray nozzle, is inserted. Material pressure is adjusted in a range of 0.08 to 0.15 mbar. Stents to be coated are mounted on a rotating mandrel so that the stents rotate at a speed of about 20-30 rotations per minute. The spray nozzle is then activated for a time in a range of 30 seconds to 6 minutes, more preferably 2 to 3 minutes, to coat the stents, depending upon the stent type and viscosity of the solutions used. After finishing spraying, the stent is removed from the mandrel and weighed while wet to obtain a "wet weight after spraying" of approximately 120 to 130% of the target amount.

The coated stents are replaced on the mandrel and loaded into a vacuum oven, where they are dried for 1 to 10 hours at 2 mbar and 40° C. After drying, the oven is flooded with nitrogen and the stents then are placed in a desiccator for 15 minutes for cooling to room temperature. Stents are again weighed to obtain a "weight after spraying" and that value is documented. The stents then are stored in the labelled mini reaction cups.

Figure 9:
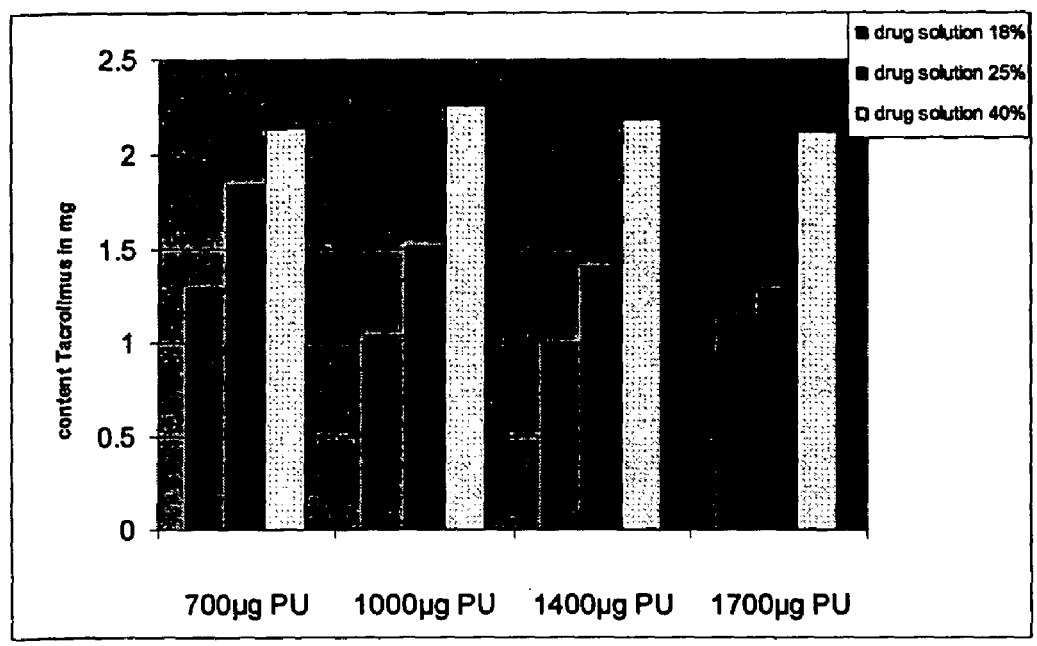
FIG. 9 shows the amount of FK506 absorbed by a polyurethane coating as a function of the concentration of the dipping solution.

In a final step, the coated stents are loaded with FK506 and optionally, other active agents. Specifically, after drying, the polymer-coated stents are dipped in the drug solution. Preferably, the active agent is dissolved in the solvent mentioned above to yield a concentration of 5 to 40%. The stent is dipped in the drug solution for between 5 and 120 seconds, depending upon the polymer coating and the solvent system used. FIG. 9 shows the amount of FK506 absorbed by a polyurethane coating as a function of the concentration of the dipping solution.

Alternatively, a polymer solution is prepared as described above, and an active agent selected from the list described hereinabove is added; the resulting drug/polymer solution is "vortexed". Typical values for the drug to polymer ratio are 0.250, 0.429, 0.667 and 1. In this case the above-described step of dipping the stent in a solution of active agent is omitted.

Example 11

Method of Brush Loading Implants with FK506

In accordance with this aspect of the present invention, a precise amount of drugs (as solutions) may be deposited on implant surfaces, wherein exact dosing is achieved using conventional dosing systems, e.g., pipettes, pumps, etc. Distribution of the solution on the implant surface may be achieved manually or automatically. This method also may be used to deposit a top-coat of drug on already drug-loaded stents (e.g., as manufactured in accordance with the methods of Example 10).

First, the implant (e.g., catheter, pre-mounted system or stent) is mounted in a rotation device, such as a rotating mandrel or opposing elastomeric wheels so that the implant is oriented with its longitudinal axis parallel to the axis of rotation. An exact amount of a drug containing solution (preferably ethanol or other solvents with low toxicity) with a defined concentration then is applied to the surface of the device by micro dosing methods (pipettes, pumps, etc.).

optionally, if the application of the drug solution is performed manually, such as by pipette, binoculars may be used to confirm deposition of the solution.

Thereafter, the applied amount of solution (e.g. drop) is manually distributed as evenly as possible over the entire surface, or a desired portion thereof, of the implant using a nylon thread, brush or roller until the solvent evaporates. Preferably, to prevent the deposited active agent from forming crystals on the implant surface, the brush-loaded device is rotated over a solvent steam (e.g. ethanol, heated to 60° C.) to enhance the uniformity of the drug layer. Finally the active agent loaded implants are dried overnight at 40° C. Applications of varying drug amounts on pre-mounted stent systems, that is, where the stent is already compressed onto the balloon of the delivery system, leads to a drug distribution of ~30% of the active agent being deposited on the stent and ~70% of the active agent being deposited on the balloon.

\* \* \*

The foregoing is merely illustrative of the principles of this invention and various modifications can be made by those skilled in the art without departing from the scope and spirit of the invention.

What is claimed is:

1. A method of treating and/or preventing restenosis in a blood vessel, the method comprising:
providing an implant including an elongate member having one or more recesses formed in a surface thereof so as to provide one or more reservoirs and having an effective amount of FK506 (tacrolimus) for treating and/or preventing restenosis, the effective amount including a multi-stage release portion of FK506 (tacrolimus) disposed in the one or more internal reservoirs, the multi-stage release portion in communication with an exterior of the implant;
inserting the implant into a vessel;
expanding the implant into contact with a wall of the vessel;
eluting FK506 from the plurality of internal lumen reservoirs into the wall of the vessel in the vicinity of the implant in an amount sufficient for treating and/or preventing restenosis in the blood vessel, the effective amount of FK506 eluted by the implant for treating and/or preventing restenosis producing a blood concentration of FK506 that ranges from about:
about 7 ng/ml to about 17 ng/ml of blood at one hour after implantation of the implant;
about 6 ng/ml to about 11 ng/ml of blood at eight hours after implantation of the implant; and/or
about 2 ng/ml to about 4 ng/ml of blood twenty-four hours after implantation of the implant.

2. The method as in claim 1, wherein the implant comprises:
an effective amount FK506 for treating and/or preventing restenosis in a blood vessel in a subject, the FK506 being in chemically covalently bound or noncovalently bound or physically immobilized form, the FK506 being disposed in the one or more internal lumen reservoirs.

3. The method of claim 2, wherein the at least one closed or perforated layer or surface comprises a metal or metal alloy.

4. The method of claim 3, wherein the metal or metal alloy has a lattice-like structure.

5. The method of claim 3, further comprising a layer or surface coating of polymer disposed on the metal or metal alloy.

6. The method of claim 5, wherein the polymer is selected from the group consisting of: Dacron, polytetrafluoroethylene, polyurethane, methacrylate polymers, a hydrogel or hydrogel/polyurethane blend.

7. The method of claim 2, wherein the at least one closed or perforated layer or surface comprises a polymer.

8. The method of claim 2, wherein the implant is selected from the group consisting of: a stent, a stent graft, a graft, a graft connector, a guide wire, a catheter or a catheter pump.

9. The method of claim 2, wherein the FK506 is loaded in nanoparticles or liposomes.

10. The method of claim 2, wherein the FK506 is applied by spraying, brush-loading or dipping.

11. The method of claim 2, wherein the FK506 is released after implantation of the implant.

12. The method of claim 11, further comprising a delayed release of the FK506.

13. The method of claim 12, wherein the delayed release of the FK506 from the implant occurs over a period ranging from 24 hr to more than 96 hr after implantation.

14. The method of claim 11, wherein release of the FK506 occurs in multiple stages.

15. The method of claim 2, further comprising at least one other pharmaceutically active agent.

16. The method of claim 15, wherein the pharmaceutically active agent is selected from the group consisting of: molsidomine, linsidomine, sodium nitroprusside, nitroglycerin or general NO donors; stimulators of soluble guanylate cyclase (sGC), BAY 41-2272 (5-cyclopropyl-2-[1-fluorobenzyl)-1H-pyrazolo [3, 4-n] pyridine-3-yl] pyrimidin-4-ylamine); hydralazine, verapamil, diltiazem, nifedipine, nimodipine or other $Ca^n$ channel blockers; captopril, enalapril, lisinopril, quinapril or other inhibitors of angiotensin converting enzymes (angiotensin converting enzyme inhibitors); losartan, candesartan, irbesartan, valsartan or other antagonists of the angiotensin II receptor; dexamethasone, betamethasone, prednisone or other corticosteroids; 17-beta-esradiol;
cyclosporin; mycophenolic acid; VEGF, VEGF receptor activators; tranilast; meloxicam, celebrex, vioxx or other COX-2 antagonists; indomethacin, diclofenac, ibuprofen, naproxen or other COX-1 inhibitors; inhibitors of plasminogen activator 1 (plasminogen activator inhibitors-1) or serpins; thrombin inhibitors, hirudin, hirulog, agratroban, PPACK; interleukin-10; sirolimus, rapamycin derivatives; PDGF antagonists; paclitaxel or 7-hexanoyl-taxol; cisplatin; vinblastine; mitoxantrone; combretastatin A4; topotecan; methotrexate; flavopiridol; actinomycin D; Rheopro/abciximab or probucol.

17. The method as in claim 1, wherein the implant comprises:
at least one closed or perforated layer or surface comprising a metal or metal alloy; and
an effective amount FK506 for treating and/or preventing restenosis in a blood vessel in a subject, the FK506 being in chemically covalently bound or noncovalently bound or physically immobilized form, wherein the metal or metal alloy further comprises a ceramic coating to which the FK506 is bound,
wherein the effective amount of FK506 (tacrolimus) covalently bound or noncovalently bound or physically immobilized on the implant ranges from about 10 μg/cm of the implant to about 200 μg/cm of the implant.

18. The method of claim 17, the implant furthercomprising a polymeric layer that completely or partly covers the ceramic coating.

19. The method of claim 18, wherein the polymeric coating is selected from the group consisting of: methacrylate polymers, polyurethane, PTFE, a hydrogel or hydrogel/polyurethane blend.

20. The method of claim 1, further comprising one or more openings formed in an outer surface of the implant and a biodegradable polymeric material disposed to at least partially seal the one or more openings formed in the outer surface of the implant.

21. The method as in claim 1, wherein the implant comprises:
at least one closed or perforated layer or surface comprising a polymer; and
an effective amount FK506 for treating and/or preventing restenosis in a blood vessel in a subject, the FK506 being in chemically covalently bound or noncovalently bound or physically immobilized form, wherein the FK506 has been dissolved in a polymerization material before the formation of the at least one closed or perforated layer or surface,
wherein the effective amount of FK506 (tacrolimus) covalently bound or noncovalently bound or physically immobilized on the implant ranges from about 10 μg/cm of the implant to about 200 μg/cm of the implant.

22. The method of claim 1, wherein the implant is characterized by at least one of the following:
the FK506 is released after implantation of the implant;
the release of FK506 is delayed after implantation of the implant;
the FK506 is released from the implant over a period ranging from 24 hr to more than 96 hr after implantation; or
release of the FK506 occurs in multiple stages.

23. The method of claim 1, wherein the implant is characterized by at least one of the following:
the implant having at least one closed or perforated layer or surface having one or more internal lumen reservoirs therein, wherein the FK506 is combined with a polymer and disposed in the one or more internal lumen reservoirs.

24. The method of claim 1, wherein the effective amount of FK506 (tacrolimus) disposed on the implant for treating and/or preventing restenosis ranges from about 10 μg/cm of the implant to about 200 μg/cm of the implant.

25. The method of claim 1, wherein the effective amount of FK506 eluted by the implant produces at least a 53% reduction in neointima formation and a detectable decrease in formation of inflammation foci following insertion of the implant into the vessel.

26. A method of treating and/or preventing restenosis in a blood vessel, the method comprising:
providing an implant including an elongate member having one or more internal reservoirs, the internal reservoir formed from a tubular wire and having an effective amount of FK506 (tacrolimus) for treating and/or preventing restenosis, the effective amount including a multi-stage release, a long-term release portion of FK506 (tacrolimus) being disposed in the one or more internal reservoirs in communication with an outer surface of the implant via one or more openings formed in the tubular wire and a rapid release portion of FK506 (tacrolimus) being disposed in an overcoat layer formed over the elongate member of the implant,
wherein, the effective amount of FK506 (tacrolimus) in the rapid release portion and the long-term release portion ranges from about 10 μg/cm of the implant to about 200 μg/cm of the implant;
inserting the implant into a vessel;
expanding the implant into contact with a wall of the vessel;
eluting FK506 from the one or more internal lumen reservoirs and/or the overcoat layer into the wall of the vessel in the vicinity of the implant in an amount sufficient for treating and/or preventing restenosis in the blood vessel, elution of the rapid release portion of the FK506 (tacrolimus) occurring over a first period of time of about 0 to about 2 days after implantation and elution of the long-term release portion of the FK506 (tacrolimus) occurring over a second period of time of about 2 days to about 21 days after implantation, and the multi-stage release including producing a blood concentration of FK506 that ranges from about:
7 ng/ml to about 17 ng/ml of blood at one hour after implantation of the implant; and
about 6 ng/ml to about 11 ng/ml of blood at eight hours after implantation of the implant.

27. The method of claim 26, wherein the implant is selected from the group consisting of: a stent, a stent graft, a graft, a graft connector, a guide wire, a catheter or a catheter pump.

28. The method of claim 26, the overcoat layer including at least one material capable of inhibiting release from the continued release portion during the first period of time.

29. The method of claim 26, the implant being a stent having a plurality of struts and the one or more internal reservoirs being laser-cut into the at least a subset of the plurality of struts.

* * * * *